United States Patent [19]

Sanborn

[11] 4,346,092
[45] Aug. 24, 1982

[54] INSECTICIDAL COMBINATIONS
[75] Inventor: James R. Sanborn, Modesto, Calif.
[73] Assignee: Shell Oil Company, Houston, Tex.
[21] Appl. No.: 311,849
[22] Filed: Oct. 16, 1981

Related U.S. Application Data

[63] Continuation-in-part of Ser. No. 153,285, May 27, 1980, abandoned, which is a continuation-in-part of Ser. No. 93,348, Nov. 13, 1979, abandoned.
[51] Int. Cl.$^3$ .................. A01N 37/10; A01N 37/34; A01N 43/42
[52] U.S. Cl. .................................. 424/258; 424/304; 424/308
[58] Field of Search ........................ 424/258, 304, 308

[56] References Cited

U.S. PATENT DOCUMENTS 4,062,968 12/1977 Fujimoto et al. ................... 424/304

OTHER PUBLICATIONS

Schneider et al.; C.A., vol. 54, 3423d (1960).

*Primary Examiner*—Allen J. Robinson

[57] ABSTRACT

Insecticidal combinations of 3,4-dihydro-2-(2-propynyl)isocarbostyril and certain pyrethroid insecticides.

2 Claims, No Drawings

INSECTICIDAL COMBINATIONS

This application is a continuation-in-part of application Ser. No. 153,285, filed on May 27, 1980, abandoned, which was a continuation-in-part of application Ser. No. 93,348, filed on Nov. 13, 1979, abandoned.

BACKGROUND OF THE INVENTION

Certain 3-phenoxybenzyl esters of cyclopropanecarboxylic acids and of α-isopropylphenylacetic acids are generally referred to as "pyrethroids", being characterized by the common properties of rapid action on insects, i.e., they are "quick knockdown agents", and low mammalian toxicity. However, while such compounds are desirable insecticides, they tend to be difficult and expensive to manufacture, because of their relatively complex chemical structures. Consequently, it is desirable to minimize the amount of such pyrethroid that is required to control the insects.

DESCRIPTION OF THE INVENTION

It has been found that 3,4-dihydro-2-(2-propynyl)isocarbostyril, of the formula:

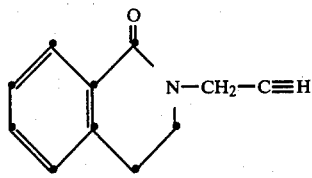

(Compound I, hereinafter, for brevity) synergizes the insecticidal activity of certain pyrethroid insecticides. The invention accordingly is the combinations of Compound I and the pyrethroid insecticides, and the use of such combinations as insecticides.

Compound I was prepared according to the procedures described by Schneider, W. and Müller, B., Arch. Pharm. 291/63, 560–566 (1958) as described in the following example. Its identity and the identity of the intermediate, were confirmed by appropriate chemical and spectral analyses.

A solution of 13.6 g of ethyl α-cyano-o-toluate and 1.3 ml of triethylamine in 130 ml of ethanol containing approximately 7 g of Raney nickel was hydrogenated in a Parr shaker at 45–50 p.s.i.g. hydrogen pressure and 55°–60° C. After 24 hours, 2 g of fresh catalyst was added and the mixture was hydrogenated for a further 24 hours.

The resulting mixture was filtered, and the solvent was evaporated from the filtrate under reduced pressure. The residue was distilled under vacuum (0.3 Torr.) to give two viscous colorless oils, one boiling at 134°–141° C. and the other boiling at 141°–142° C. These fractions were combined and triturated with hexane to give 3,4-dihydroisocarbostyril (A), as a white solid, m.p.: 58°–60° C.

2.1 g of sodium hydride (59% mineral oil dispersion) was washed with hexane to remove the oil and then suspended in 50 ml of xylene. A solution of 7.4 g of A in 30 ml of xylene was added thereto drop-by-drop. The resulting mixture was stirred for 20 minutes at room temperature, then the mixture was refluxed for 1.75 hours. The mixture was cooled, a solution of 10 g of propargyl bromide in 24 ml of xylene was added drop-by-drop. The resulting mixture was stirred at room temperature for 20 minutes, then was slowly heated to reflux and was refluxed for 1 hour. While still hot, the resulting mixture was filtered through celite and the solvent was evaporated under reduced pressure. The residue was chromatographed over silica gel, using ethyl acetate as eluant. The product was reabsorbed on silica gel, and washed with approximately one liter of hexane. The resulting single band was extracted with acetone, and the solvent was evaporated under reduced pressure to give Compound I, as an amber oil.

The pyrethroids contemplated in this invention can be defined by the general formula:

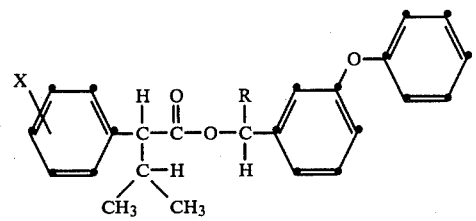

wherein R is hydrogen or cyano (—CN), and X is chlorine, bromine, fluorine, or difluoromethoxy or is alkoxy of from one to four carbon atoms.

A preferred pyrethroid of this class of Compound B, described hereinafter.

These pyrethroids can exist in the form of optical isomers. This invention contemplates the use of each of the insecticidally active isomers, as well as racemic mixtures, and other mixtures of isomers of one or more of the insecticidally active pyrethroids. The various isomers of such compounds may have different insecticidal activities and/or knockdown potency. Accordingly, one may prefer to resolve mixtures of isomers to recover a more insecticidally active isomer or racemic mixture or to prepare the more active forms directly, and use it or them in the compositions of the invention.

Such pyrethroids and methods for their preparation are disclosed in U.S. Pat. No. 4,062,968.

Suitably, from abou 0.002 to about 0.05 parts by weight of Compound I are used per part by weight of the pyrethroid; preferably, the weight ratio, Compound I/pyrethroid, lies within the range of from about 0.005 to 0.025/1.

The synergistic effect of Compound I upon such pyrethroids was determined as follows:

Fifty 4–5 day-old houseflies (*Musca domestica* (Linne)) were placed in a cage and sprayed with a standard amount of a standardized solution of the test material. The flies then were transferred to a cage containing a milk pad for food. The flies were held for 18–20 hours and mortality counts (the number of dead and moribund flies) were made. The tests were conducted using several different dosage rates for each test material. The data were plotted on log probit paper and the $LC_{50}$ dosage (dosage required to give 50% mortality) in each case was determined.

The following materials were tested:

| Material | Identity |
| --- | --- |
| A | Compound I |
| Compound B | (±)R,S,-alpha-cyano-3-phenoxybenzyl (±)-R,S,-alpha-isopropyl-p-chlorophenylacetate. |
| C | Combination, Compound B + 1% by weight of |

-continued

| Material | Identity |
|---|---|
| | Compound I. |

The synergistic ratio (LC$_{50}$ of combination/LC$_{50}$ pyrethroid alone) was determined in each case.
The results were as follows:

| Test Material | LC$_{50}$ Dosage | Synergistic Ratio |
|---|---|---|
| None | 0 | — |
| A | >1 | — |
| B | .0035 | — |
| C | .00032 | 11.0 |

This invention includes a method for killing insects which comprises subjecting the insects to the effect of a lethal dosage of one of the combinations of the invention—as by applying the combination to the insects and/or the locus to be protected from the insects. Also, the invention includes insecticidal compositions containing an effective amount of a combination of the invention together with an inert carrier or a surface-active agent, or both.

The term "carrier" as used herein means an inert solid or fluid material, which may be inorganic or organic and of synthetic or natural origin, with which the active material is mixed or formulated to facilitate its application to the plant, seed, soil or other subject to be treated, or its storage, transport or handling.

Suitable solid carriers are natural and synthetic clays and silicates, for example, natural silicas such as diatomaceous earths; magnesium silicates, for example, talcs, magnesium aluminum silicates, for example, kaolinites, montmorillonites and micas; calcium carbonates; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols; bitumen, waxes such as, for example, beeswax, paraffin wax, and chlorinated mineral waxes; and solid fertilizers, for example, superphosphates.

Examples of suitable fluid carriers are water, alcohols, such as, for example, isopropanol, glycols; ketones such as, for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquefied normally vaporous gaseous compounds. Mixtures of different liquids are often suitable. The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent, 15% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing ½–10% by weight of toxicant. Granules are usually prepared to have a size between 10 and 100 BS mesh (1.676–0.152 mm), and may be manufactured by agglomeration or impregnation techniques. Generally, granules will contain ½–25% by weight toxicant and 0–1% by weight of additives such as stabilizers, slow release modifiers and binding agents. Emulsifiable concentrates usually contain, in addition to the solvent and, when necessary, cosolvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight toxicant, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may also contain other ingredients, for example, other compounds possessing pesticidal, especially insecticidal, acaricidal, herbicidal or fungicidal properties.

The method of applying a combination to control insects comprises applying the combination, ordinarily in a composition of one of the aforementioned types, to a locus or area to be protected from the insects, such as the foliage and/or fruit of plants. The composition, of course, is applied in an amount sufficient to exert the desired action. This dosage is dependent upon many factors, including the species of insect(s) to be controlled, the carrier employed, the method and conditions of the application, whether the composition is present at the locus in the form of an aerosol, or as a film, or as discrete particles, the thickness of film or size of particles, and the like, proper consideration and resolution of these factors to provide the necessary dosage of the active material at the locus to be protected being within the skill of those versed in the art. In general, however, the effective dosage of a combination of the invention is at the locus to be protected—i.e., the dosage which the insects contacts—is of the order of 0.001 to 0.5% based on the total weight of the composition, though under some circumstances the effective concentration will be as little as 0.0001% or as much as 2%, on the same basis.

I claim:

1. An insecticidal composition containing as active ingredient a combination of
   (a) 3,4-dihydro-2-(2-pyropynyl)isocarbostyril, and
   (b) a pyrethroid of the formula

wherein R is hydrogen or cyano (—CN), and X is chlorine, bromine, fluorine, difluoromethoxy, or alkoxy of from one to four carbon atoms, in the proportion of from about 0.002 to about 0.05 part by weight of (a) per part by weight of (b).

2. A composition according to claim 1 wherein the pyrethroid is (±)-R,S,-alpha-cyano-3-phenoxybenzyl (±)-R,S-alpha-isopropyl-p-chlorophenylacetate.